US012016733B2

(12) United States Patent
Ward et al.

(10) Patent No.: US 12,016,733 B2
(45) Date of Patent: *Jun. 25, 2024

(54) FORCEPS WITH TISSUE STOPS

(71) Applicant: GYRUS ACMI, INC., Southborough, MA (US)

(72) Inventors: Zane R. Ward, Minneapolis, MN (US); Todd W. Sharratt, Stillwater, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 1036 days.

This patent is subject to a terminal disclaimer.

(21) Appl. No.: 16/884,382

(22) Filed: May 27, 2020

(65) Prior Publication Data

US 2020/0281683 A1 Sep. 10, 2020

Related U.S. Application Data

(63) Continuation of application No. 15/403,515, filed on Jan. 11, 2017, now Pat. No. 10,722,317.

(Continued)

(51) Int. Cl.
*A61B 18/18* (2006.01)
*A61B 17/28* (2006.01)
(Continued)

(52) U.S. Cl.
CPC ............ *A61B 90/03* (2016.02); *A61B 17/282* (2013.01); *A61B 17/2841* (2013.01);
(Continued)

(58) Field of Classification Search
CPC . A61B 17/282; A61B 17/2841; A61B 17/285; A61B 17/29; A61B 17/2909;
(Continued)

(56) References Cited

U.S. PATENT DOCUMENTS 2,114,695 A    4/1938   Anderson
2,137,710 A    11/1938   Anderson
(Continued)

FOREIGN PATENT DOCUMENTS

CN    101803938 A    8/2010
CN    103690214 A    4/2014
(Continued)

OTHER PUBLICATIONS

"Chinese Application Serial No. 201780004943.3, Office Action dated Jun. 8, 2020", w/ English translation, 22 pgs.
(Continued)

*Primary Examiner* — Michael F Peffley
*Assistant Examiner* — Amanda L Zink
(74) *Attorney, Agent, or Firm* — Schwegman Lundberg & Woessner, P.A.

(57) ABSTRACT

An instrument that includes forceps. The forceps include a jaw assembly. The jaw assembly includes a first jaw and a second jaw. The first jaw includes a gripping section, and the second jaw includes a gripping section. The jaw assembly is moveable between an open position and a closed position. The first jaw is electrically conductive, the second jaw is electrically conductive, or both the first jaw and the second jaw are electrically conductive. The first jaw includes a first tissue stop that is centered on a medial plane of the first jaw. The tissue stop extends from the first jaw towards the second jaw. The first tissue stop is adapted to block an anatomical feature from extending beyond a proximal end of the gripping section of the first jaw, a proximal end of the gripping section of the second jaw, or both.

19 Claims, 4 Drawing Sheets

Related U.S. Application Data

(60) Provisional application No. 62/277,037, filed on Jan. 11, 2016.

(51) Int. Cl.

| | | |
|---|---|---|
| *A61B 17/29* | (2006.01) | |
| *A61B 18/08* | (2006.01) | |
| *A61B 18/14* | (2006.01) | |
| *A61B 90/00* | (2016.01) | |
| A61B 17/00 | (2006.01) | |
| A61B 17/285 | (2006.01) | |
| A61B 17/295 | (2006.01) | |
| A61B 18/00 | (2006.01) | |
| A61B 18/12 | (2006.01) | |

(52) U.S. Cl.
CPC .......... *A61B 17/29* (2013.01); *A61B 17/2909* (2013.01); *A61B 18/085* (2013.01); *A61B 18/1442* (2013.01); *A61B 18/1445* (2013.01); A61B 2017/00371 (2013.01); A61B 2017/2825 (2013.01); *A61B 17/285* (2013.01); *A61B 2017/2926* (2013.01); *A61B 17/295* (2013.01); *A61B 2018/00083* (2013.01); *A61B 2018/00404* (2013.01); *A61B 2018/00589* (2013.01); *A61B 2018/00601* (2013.01); *A61B 2018/00607* (2013.01); *A61B 2018/0063* (2013.01); *A61B 18/1206* (2013.01); *A61B 2018/126* (2013.01); *A61B 2018/1455* (2013.01); *A61B 2090/036* (2016.02)

(58) Field of Classification Search
CPC . A61B 17/295; A61B 18/085; A61B 18/1206; A61B 18/1442; A61B 18/1445; A61B 2017/00371; A61B 2017/2825; A61B 2017/2926; A61B 2018/00083; A61B 2018/00404; A61B 2018/00589; A61B 2018/00601; A61B 2018/00607; A61B 2018/0063; A61B 2018/126; A61B 2018/1455; A61B 2090/036; A61B 90/03
See application file for complete search history.

(56) References Cited

U.S. PATENT DOCUMENTS

| | | | |
|---|---|---|---|
| 3,911,923 A | 10/1975 | Yoon | |
| 3,920,021 A | 11/1975 | Hiltebrandt | |
| 3,934,589 A | 1/1976 | Zimmer | |
| 3,938,527 A | 2/1976 | Rioux et al. | |
| 4,003,380 A | 1/1977 | Wien | |
| 4,005,714 A | 2/1977 | Hiltebrandt | |
| 4,016,881 A | 4/1977 | Rioux et al. | |
| 4,054,143 A | 10/1977 | Bauer | |
| 4,085,756 A | 4/1978 | Weaver | |
| 4,171,715 A | 10/1979 | Forsstrom | |
| 4,393,872 A | 7/1983 | Reznik et al. | |
| 4,418,692 A | 12/1983 | Guay | |
| 4,671,274 A | 6/1987 | Sorochenko | |
| 5,147,378 A | 9/1992 | Markham | |
| 5,222,973 A | 6/1993 | Sharpe et al. | |
| 5,258,006 A | 11/1993 | Rydell et al. | |
| 5,308,576 A * | 5/1994 | Green | A61B 17/07207 419/36 |
| 5,445,638 A | 8/1995 | Rydell et al. | |
| 5,458,598 A | 10/1995 | Feinberg et al. | |
| 5,527,313 A | 6/1996 | Scott et al. | |
| 5,562,702 A | 10/1996 | Huitema et al. | |
| 5,569,269 A | 10/1996 | Hart et al. | |
| 5,607,436 A * | 3/1997 | Pratt | A61B 17/1285 606/139 |
| 5,725,536 A * | 3/1998 | Oberlin | A61B 17/07207 606/139 |
| 5,735,849 A | 4/1998 | Baden et al. | |
| 5,797,938 A * | 8/1998 | Paraschac | A61B 18/1445 606/177 |
| 5,833,700 A * | 11/1998 | Fogelberg | A61B 17/1285 606/151 |
| 6,419,675 B1 | 7/2002 | Gallo, Sr. | |
| 6,458,130 B1 | 10/2002 | Frazier et al. | |
| 6,605,104 B2 | 8/2003 | Sato et al. | |
| 7,131,971 B2 | 11/2006 | Dycus et al. | |
| 8,663,270 B2 | 3/2014 | Donnigan et al. | |
| 9,339,327 B2 | 5/2016 | Koss | |
| 10,485,566 B2 | 11/2019 | Nelson et al. | |
| 10,722,317 B2 | 7/2020 | Ward et al. | |
| 2005/0021062 A1* | 1/2005 | Dennis | A61B 17/1227 606/157 |
| 2010/0063528 A1 | 3/2010 | Beaupre | |
| 2012/0080474 A1* | 4/2012 | Farascioni | A61B 17/068 227/175.1 |
| 2013/0345702 A1 | 12/2013 | Wandel | |
| 2014/0135804 A1* | 5/2014 | Weisenburgh, II | A61B 17/29 606/169 |
| 2014/0257285 A1* | 9/2014 | Moua | A61B 17/282 606/52 |
| 2015/0209103 A1 | 7/2015 | Artale et al. | |
| 2016/0143687 A1* | 5/2016 | Hart | A61B 18/1442 29/525 |
| 2016/0157923 A1* | 6/2016 | Ding | A61B 17/2812 606/51 |
| 2017/0196648 A1 | 7/2017 | Ward et al. | |
| 2017/0238990 A1 | 8/2017 | Soni | |
| 2018/0161112 A1 | 6/2018 | Weir et al. | |
| 2020/0305965 A1 | 10/2020 | Pham et al. | |

FOREIGN PATENT DOCUMENTS

| | | |
|---|---|---|
| CN | 104095680 A | 10/2014 |
| CN | 108430350 A | 8/2018 |
| CN | 108430350 B | 6/2021 |
| CN | 113274123 A | 8/2021 |
| EP | 0765639 A1 | 4/1997 |
| EP | 1813209 A1 | 8/2007 |
| EP | 2777587 A1 | 9/2014 |
| WO | WO-2015017995 A1 | 2/2015 |
| WO | WO-2017123584 A1 | 7/2017 |

OTHER PUBLICATIONS

"Chinese Application Serial No. 201780004943.3, Office Action dated Dec. 17, 2020", with English translation, 7 pgs.

"Chinese Application Serial No. 201780004943.3, Response filed Jan. 27, 2021 to Office Action dated Dec. 17, 2020", w/ English Claims, 16 pgs.

"Chinese Application Serial No. 201780004943.3, Response filed Feb. 18, 2021 to Telephone Consultation on Feb. 17, 2021", with English translation of claims and machine translation, 71 pgs.

"Chinese Application Serial No. 201780004943.3, Response filed Sep. 22, 2020 to Office Action dated Jun. 8, 2020", w/ English Claims, 20 pgs.

"U.S. Appl. No. 15/403,515, Corrected Notice of Allowability dated May 12, 2020", 2 pgs.

"U.S. Appl. No. 15/403,515, Non Final Office Action dated Nov. 26, 2019", 12 pgs.

"U.S. Appl. No. 15/403,515, Notice of Allowance dated Mar. 18, 2020", 6 pgs.

"U.S. Appl. No. 15/403,515, Response filed Feb. 26, 2020 to Non Final Office Action dated Nov. 26, 2019", 12 pgs.

"International Application Serial No. PCT/US2017/012933, International Preliminary Report on Patentability dated Jul. 26, 2018", 10 pgs.

"International Application Serial No. PCT/US2017/012933, International Search Report dated Mar. 27, 2017", 4 pgs.

"International Application Serial No. PCT/US2017/012933, Written Opinion dated Mar. 27, 2017", 8 pgs.

"U.S. Appl. No. 16/830,201, Final Office Action dated Sep. 7, 2023", 19 pgs.

(56) References Cited

OTHER PUBLICATIONS

"U.S. Appl. No. 16/830,201, Non Final Office Action dated Apr. 7, 2023", 17 pgs.
"U.S. Appl. No. 16/830,201, Response filed May 15, 2023 to Non Final Office Action dated Apr. 7, 2023", 14 pgs.
"U.S. Appl. No. 16/830,201, Advisory Action dated Oct. 11, 2023", 4 pgs.
"U.S. Appl. No. 16/830,201, Response filed Oct. 2, 2023 to Final Office Action dated Sep. 7, 2023", 12 pgs.
"U.S. Appl. No. 16/830,201, Response filed Nov. 28, 2023 to Advisory Action dated Oct. 11, 2023", 12 pgs.
"Chinese Application Serial No. 202110545109.3, Office Action dated Oct. 23, 2023", W/English Translation, 17 pgs.

* cited by examiner

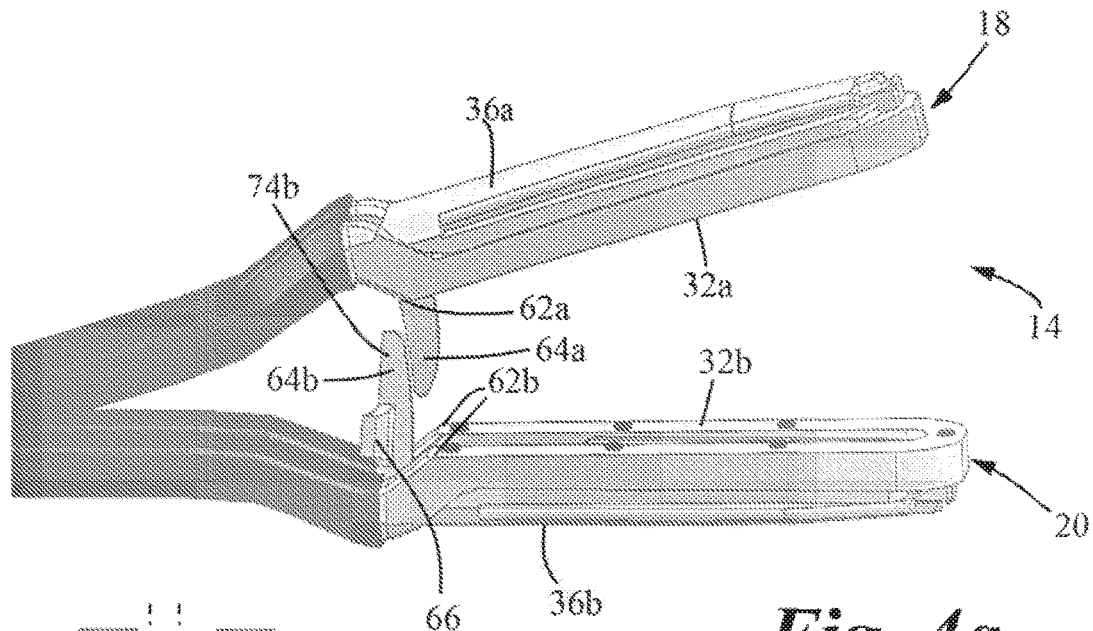
*Fig. 4a*
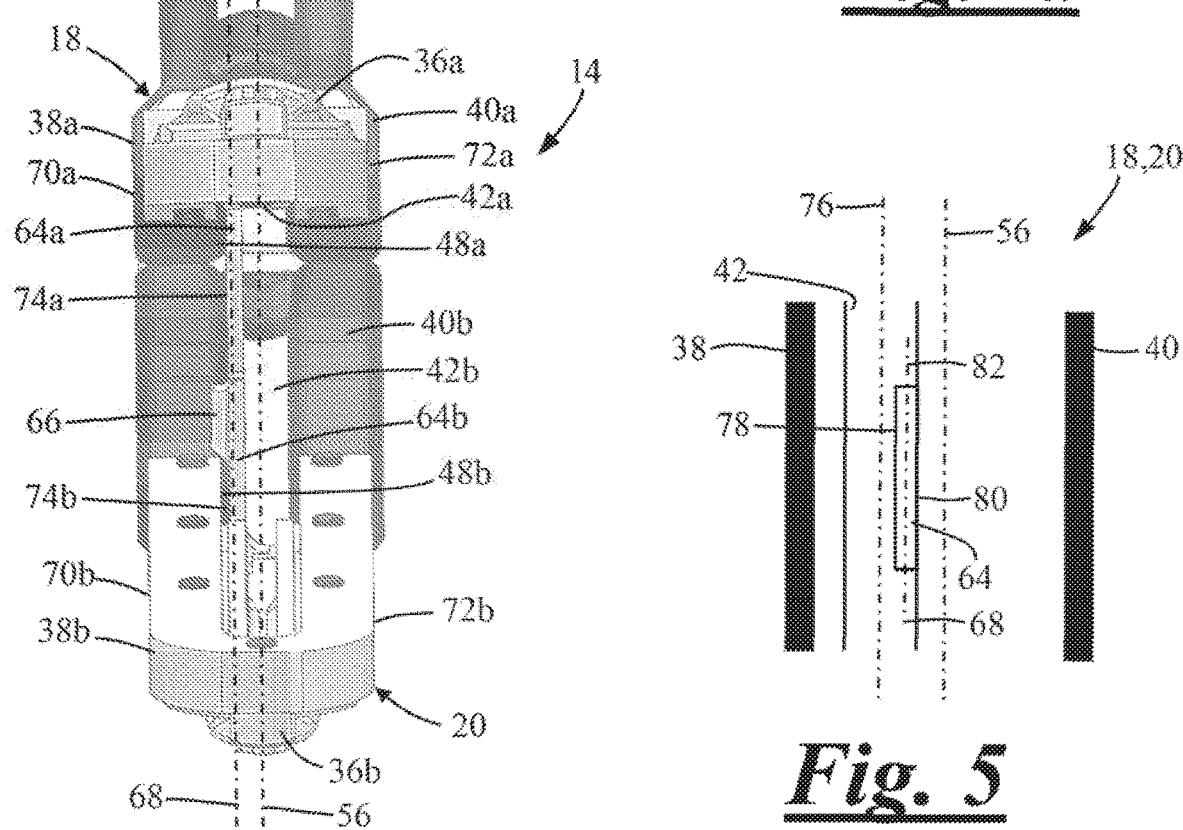
*Fig. 4b*
*Fig. 5*

FORCEPS WITH TISSUE STOPS

CROSS-REFERENCE TO RELATED APPLICATIONS

This application is a Continuation of U.S. patent application Ser. No. 15/403,515, filed on Jan. 11, 2017, which claims the benefit of U.S. Provisional Patent Application Serial No. 62/277,037, filed on Jan. 11, 2016, the contents of which are incorporated herein by reference in their entirities.

FIELD

These teachings relate to an instrument, and more particularly to forceps that include one or more tissue stops.

BACKGROUND

Forceps are plier-like instruments that have opposing jaws. The jaws can be used during a medical procedure to effect an anatomical feature, such as a vessel or tissue. For example, a vessel or tissue can be positioned between the gripping sections of the opposing jaws, and the jaws can be used to move, grip, grasp, push, pull, cut, dissect and/or otherwise effect the vessel or tissue. Some forceps also include electrosurgical capabilities for electrically effecting an anatomical feature. For example, a vessel or tissue can be sealed or coagulated with an electrosurgical therapy current that is passed from or between one or both of the jaws.

Before effecting the anatomical feature, care should be taken to properly position or locate the anatomical feature between the gripping sections of the opposing jaws. For example, if a vessel or tissue is positioned or located between the jaws too far in a proximal direction, for example beyond a proximal end of the griping sections, the vessel or tissue may not be held or gripped securely, which may undesirably cause trauma to the anatomical feature while being effected. Moreover, some forceps have a hinge or other pivot mechanism that allows for the one or both of the jaws to move towards and away from one another. A vessel or tissue that is positioned too far in a proximal direction may be pinched in the hinge or pivot mechanism, which may undesirably cause bleeding or trauma to the anatomical feature.

Further, while using electrosurgical forceps, if a vessel or tissue is positioned too far in a proximal direction, for example beyond the electrically conductive sections of one or both of the jaws, that portion of the vessel or tissue may not be sufficiently sealed or coagulated. Advancing a cut blade onto or through a portion of a vessel or tissue that is not sufficiently coagulated may undesirably cause bleeding or trauma to the anatomical feature.

A need for improvement in the art is therefore apparent. For example, it may be desirable to provide forceps that include one or more features that can assist a surgeon in positioning an anatomical feature between the jaws. It may be desirable to provide forceps that include one or more features that can prevent or at least reduce chances of an anatomical feature being positioned or located too far in a proximal direction between the jaws. For example, it may be desirable to provide forceps that include one or more features that can help locate an anatomical feature between the gripping sections of the jaws and thus reduce chances of the anatomical feature being pinched in a hinge or pivot mechanism of the forceps. For example, it may be desirable to provide forceps that include one or features that can help locate an anatomical feature between the conductive sections of the jaws of electrosurgical forceps so that the entire anatomical feature can be properly sealed or coagulated.

SUMMARY

These teachings advantageously provide forceps that include one more tissue stops. The one or more tissue stops may advantageously assist a surgeon in positioning an anatomical feature between the jaws. The one or more tissue stops may block, prevent, or at least reduce chances of an anatomical feature being located too far in a proximal direction between the jaws. The one or more tissue stops may help locate an anatomical feature between the gripping sections of the jaws and thus reduce the chances of some or all of the anatomical feature being pinched in a hinge or pivot mechanism of the forceps. The one or more tissue stops may help locate an anatomical feature between the electrically conductive sections of the jaws so that the entire anatomical feature can be sufficiently coagulated during an electrosurgical procedure. By incorporating the one or more tissue stops according to the teachings herein into forceps, time spent ensuring an anatomical feature is properly positioned between the jaws may be reduced.

An instrument comprising forceps comprising a jaw assembly. The jaw assembly includes a first jaw and a second jaw. The first jaw comprises a gripping section and the second jaw comprises a griping section. The jaw assembly is moveable between an open position and a closed position. The first jaw is electrically conductive, the second jaw is electrically conductive, or both the first jaw and the second jaw are electrically conductive. The first jaw includes a first tissue stop that is centered on a medial plane of the first jaw. The first tissue stop extends from the first jaw towards the second jaw. The first tissue stop is adapted to block an anatomical feature from extending beyond a proximal end of the gripping section of the first jaw, a proximal end of the gripping section of the second jaw, or both.

An instrument comprising forceps comprising a hand piece and a jaw assembly. The jaw assembly is connected to the hand piece. The jaw assembly includes a first jaw and a second jaw. The first jaw comprises a gripping section and the second jaw comprises a griping section. The jaw assembly is moveable between an open position and a closed position. A portion of the first jaw is electrically conductive, a portion of the second jaw is electrically conductive, or a portion of both the first jaw and the second jaw are electrically conductive. The first jaw includes a first tissue stop that is centered on a medial plane of the first jaw. The first tissue stop extends from the first jaw towards the second jaw. The first tissue stop overlaps the second jaw when the jaw assembly is in the open position at a position proximal to the end of the gripping section of the first jaw, at a position proximal end of the gripping section of the second jaw, or both.

An instrument comprising forceps comprising a jaw assembly. The jaw assembly includes a first jaw and a second jaw. The first jaw comprises a gripping section and a first tissue stop, and the second jaw comprises a griping section and a slot defined between two opposing lateral edges. The first tissues top is generally U-shaped and includes an inner leg, an outer leg, and a gap defined between the inner leg and the outer leg. The inner leg is centered on a medial plane of the first jaw. The jaw assembly is moveable between an open position and a closed position. When the jaw assembly is moved to the closed position: a portion of the inner leg is received into the slot of the second jaw; a lateral side of the inner leg is juxtaposed with one of the two opposing lateral edges of the slot; a medial side of the outer leg is juxtaposed with a lateral side of the second jaw; and a portion of the second jaw is received into the gap. When the jaw assembly is in the open position, at least one of the inner leg and at least a portion of the outer leg overlaps the second jaw at a position proximal to an end of the gripping section of the first jaw, at a position proximal to an end of the gripping section of the second jaw, or both.

BRIEF DESCRIPTION OF THE DRAWINGS

FIG. 4a is a side perspective view of a jaw assembly.

FIG. 4b is a front perspective view of the jaw assembly of FIG. 5a.

FIG. 5 is a top schematic view of a jaw assembly.

DETAILED DESCRIPTION

Figure 1:
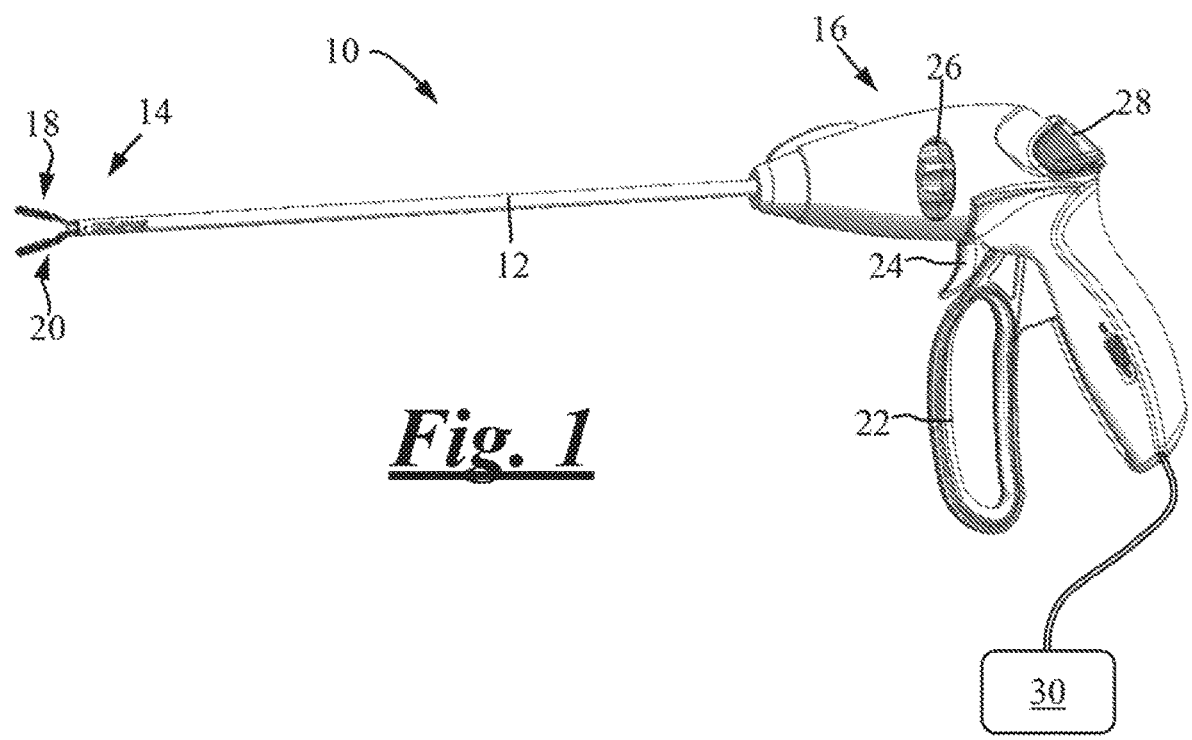
FIG. 1 is a perspective view of an instrument including a jaw assembly.

This disclosure claims the benefit of U.S. Provisional Patent Application No. 62/277,037 filed on Jan. 11, 2016, which is hereby incorporated by reference herein in its entirety for all purposes.

Instrument.

These teachings provide an instrument. The instrument can be any instrument used to effect an object. Effecting may mean, for example: manipulating, engaging, moving, grasping, gripping, pushing, pulling, cutting, tearing, coagulating, sealing, cauterizing, dissecting, fulgurating, or otherwise effecting an object or anatomical feature. The object may be any object, whether an anatomical feature or not. The anatomical feature may be, for example, a vessel, tissue, vein, artery, any portion of the anatomy, or a combination thereof.

The instrument can be used in medically related procedures or non-medically related procedures. The instrument can be used in open and/or laparoscopic or minimally invasive procedures. The instrument can be medical forceps, cutting forceps, electrosurgical forceps, bipolar forceps, the like, or a combination thereof.

The instrument may be used with or without power. When used with power, the instrument can be used in electrosurgery. The instrument can be in electrical communication with a suitable power source so that the instrument can be used in a bipolar circuit. For example, a suitable current, therapy, and/or signal provided by a power source may be passed from, though, or between, the jaws, gripping sections, electrically conductive sections, electrodes, or a combination thereof to electrically effect an anatomical feature. For example, the anatomical feature can be sealed or coagulated between the gripping sections or the electrically conductive sections of the opposing jaws with a bipolar therapy signal provided by the power source. That is, the opposing jaws of the instrument may be in communication with opposing poles of the power source so that the instrument can function as bipolar forceps and coagulate or seal an anatomical feature between the jaws. As will be discussed further below, the instrument also includes a cut blade that can be advanced through the coagulated or sealed anatomical feature.

Hand Piece.

The instrument may include a hand piece. The hand piece may function to house, support, and/or contain one or more components of the instrument. For example, the hand piece may house, support, and/or contain the parts or components required to move or actuate the jaw assembly, the one or more jaws, the cut blade, or a combination thereof. The hand piece may house, support, and/or contain the parts, components, electrical conductors or wires, required for the electrosurgical functions of the instrument. The instrument, the hand piece, or both may include sufficient controls for operating, actuating, and/or manipulating the instrument. The controls may include a wheel, a trigger, a lever, a button, the like, or a combination thereof. One or more of these controls may be manipulated or moved to open/close the jaw assembly; move one or more of the jaws towards or away from one another; rotate the jaw assembly; advance or retract the jaw assembly; advance or retract the tubular member; advance or retract a cut blade; apply a therapy current; or a combination thereof. For example, manipulation or movement of the lever may be adapted to move the jaw assembly (i.e., move one or both of the jaws) from an open position to a closed position, and vice versa. For example, manipulation or movement of the wheel may be adapted to rotate the jaw assembly about a longitudinal axis of the jaw assembly, the tubular member, or both. For example, manipulation or movement of the trigger may be adapted to translate or reciprocate the cut blade about the longitudinal axis of the cut blade, the tubular member, the jaw assembly, or a combination thereof. For example, manipulation or movement of the button may be adapted to apply a therapeutic current or signal from the power supply to the jaw assembly, one or both of the jaws, one or more of the gripping sections, one or more of the electrically conductive sections, one or more of the shims, one or more of the electrodes, or a combination thereof to electrically effect an anatomical feature.

Tubular Member.

The tubular member may function to permit a portion of the instrument to be inserted into a patient or the anatomy, while a portion of the instrument remains outside of the patient or anatomy. The tubular member may be configured to be inserted into the anatomy through a trocar. The tubular member may allow for the jaw assembly and/or one or more functional elements of the instrument to be manipulated without being impeded by a trocar, the anatomy, or both.

The tubular member may be an elongated member that extends along a longitudinal axis. The proximal end of the tubular member may be connected to the hand piece. The distal end may define a mouth or opening (i.e., a distal opening). The tubular member may be at least partially hollow and may define therein an inner portion. The hollow or inner portion of the tubular member, the distal opening, or both, may be sufficiently sized so that one or more jaws, a jaw assembly, a cut blade, one or more tissue stops, arcuate sections, or a combination thereof can be received and/or moved in the tubular member. The tubular member may be substantially straight; may include one or more angles, bends or arcs; or a combination thereof. The tubular member may be substantially rigid, substantially flexible, substantially resilient, or a combination thereof.

In some configurations, the tubular member can be moved (i.e., axially, distally, proximally, rotationally or a combination thereof) relative to the arcuate sections, the hand piece, or a combination thereof. The tubular member can be moved by manipulating one of the user controls on the hand piece. The tubular member may be movable relative to the jaw assembly, the hand piece, or both so that the jaw assembly can be moved or flexed between an open position and a closed position. More specifically, by manipulating one or more user inputs, the tubular member can be moved in a first direction (i.e., distally relative to the hand piece) and up, over and/or onto the arcuate portions of one or both of the jaws so that the jaw assembly can be moved into a closed or gripping position. Of course, by manipulating one or more user inputs, the tubular member can be moved in a second direction (i.e., proximally relative to the hand piece) so that the tubular moves off of the arcuate sections, thus allowing one or both of the jaws to relax or flex into an open, steady state position. In this type of configuration, the jaw assembly is preferably fixed to the hand piece and does not move distally or proximally relative to the hand piece.

Additionally, or alternatively, the tubular member may be fixed relative to the hand piece and the jaw assembly may be moveable. In this configuration, by manipulating one or more user inputs, the jaw assembly can be moved in a first direction (i.e., proximally towards the hand piece) so that the tubular member or the mouth or opening of the tubular members acts on the arcuate sections of one or both of the jaws so that the jaw assembly can be moved into a closed or gripping position. Similarly, by manipulating one or more user inputs, the jaw assembly can be moved in a second direction (i.e., distally towards the hand piece) so that the tubular member or the mouth or opening of the tubular members is moved off of the arcuate sections of one or both of the jaws so that the jaw assembly can relax or flex into an open position.

Jaw Assembly.

The instrument may include a jaw assembly. The jaw assembly may be configured to perform one or more effecting functions. For example, the one or more effecting functions may include: capturing an object or anatomical feature; grasping an object or anatomical feature; providing a clamping force to secure an object or anatomical feature; providing retraction of an object or anatomical feature; providing a compression force across an object or anatomical feature captured in the jaw assembly; or a combination thereof. The anatomical feature may be, for example, a vessel, tissue, vein, artery, a portion of the anatomy, or a combination thereof The jaw assembly may be used in electrosurgery to perform one or more electrically effecting functions, such as cutting, coagulating, cauterizing, dissecting, and/or fulgurating an object anatomical feature.

The jaw assembly may be moved between a closed position and an open position. More specifically, the jaw assembly may include one jaw that moves relative to the other jaw so that the jaw assembly moves between an open and closed position. The moving jaw may comprise one or more tissue stops. Additionally, or alternatively, the non-moving jaw may include one or more tissue stops. Alternatively, the jaw assembly may comprise a pair of opposing jaws that are both moved towards each other into the closed position and away from one another into the open position. In this configuration, one or both of the jaws may include one or more tissue stops.

In some configurations, the jaw assembly may be moved into a closed position by applying a force one or both of the arcuate sections of the jaws, discussed further below, which causes one or both of the jaws to move towards each other into the closed position. Conversely, the jaw assembly is preferably moved into an open position by removing a force one or both of the arcuate sections of the jaws, which causes one or both of the jaws to relax and resiliently move away from each other into the open position.

In other configurations, the jaw assembly may include a hinge or other pivot mechanism for pivoting the jaw assembly between the open and closed positions.

The closed position of the jaw assembly may be defined as a position of the jaws or the jaw assembly where virtually no gap, or only a slight gap, exists between the gripping sections, the electrically conductive sections, the jaws, or a combination thereof. In the closed position, a clamping or gripping force of the gripping sections, the electrically conductive portions, the jaws, or a combination thereof may be higher or larger than a clamping or gripping force between the gripping sections, the electrically conductive sections, the jaws, or a combination thereof when the jaws are in the open position.

The open position may be defined as a position of the jaws or the jaw assembly where a gap exists between the gripping sections, the electrically conductive portions, the jaws, or a combination thereof. In the open position, a clamping or gripping force of the gripping sections, the electrically conductive sections, the jaws, or a combination thereof may be less or lower than a clamping or gripping force between the gripping sections, the electrically conductive sections, the jaws, or a combination thereof when the jaws are in the closed position.

In a neutral or a steady state position, the jaw assembly may be in either an open position or in a closed position.

While the jaw assembly is in an open position, closed position, or in a position there between, the jaw assembly can be rotated relative to the hand piece or the tubular member by manipulating or moving one or more of the controls on the hand piece discussed above. Rotating the jaw assembly may provide for a user to alter an orientation or approach of the jaw assembly relative to an anatomical feature without having to twist or adjust the hand piece into a difficult or uncomfortable position, for example.

Jaws.

The jaw assembly may include one or more jaws. The jaws may be moved, adjusted, manipulated, repositioned, opened, closed, rotated, advanced, retracted, or otherwise articulated to perform one or more of the effecting functions discussed herein. The jaws may be moved, adjusted, manipulated, repositioned, rotated, advanced, retracted, or otherwise articulated when the jaw assembly is moved between the open and closed positions by moving or manipulating one or more of the user controls on the hand piece.

The jaws may be arranged to oppose one another. The jaws may include an upper jaw and an identical lower jaw. Alternatively, the opposing jaws need not be identical. In other words, the geometry of the upper jaw may be different from the lower jaw. For example, one of the jaws may include a flexing section having one or more arcuate sections or sections, and another one of the jaws may be free of a flexing section, one or more arcuate sections or sections. The jaws may be substantially rigid; substantially flexible; substantially resilient, or a combination thereof. That is, the jaws may have one or more sections that are substantially rigid; one or more sections that are substantially flexible; one or more sections that are substantially resilient, or a combination thereof. Preferably, at least one of the jaws or a portion thereof is bendable so that the jaw assembly can be moved between the open position and the closed position by applying a force on one or both of the jaws as was discussed above. Preferably, at least one of the jaws or portions thereof is resilient so that the jaws can be moved between the closed position and the open position by releasing a force from one or both of the jaws as was discussed above.

The jaws may be fabricated from any suitable material. Preferably, the jaws are fabricated from a material that is suitable for use in medical procedures, and is flexible, yet strong. For example, the jaw elements may be made from sheet metal or wire. The jaws may be formed by any suitable process, such as stamping, metal injection molding (MIM), or plastic injection molding, for example. The jaws may be fabricated from a material that can pass current so that one or more of the jaws can be used in electrosurgery. One or both of the jaws, or sections thereof, may be electrically conductive. One or both jaws, or sections thereof, may be non-electrically conductive. The jaws may be thermally insulating so that a thermal barrier can be provided between the jaws, the jaw assembly, or both. A thermally insulting jaw may be preferred in some applications so that thermal spread is limited or reduced. One or more sections of the jaws may be covered or coated in an insulating material so that electrical shorts can be prevented if the jaws come into contact with one another or another object or feature of the instrument or surrounding environment.

Each of the jaws may include one or more jaw sections. A jaw section as used herein may be an elongated section of a jaw that extends between the corresponding gripping and anchoring section. A jaw may include two jaw elements. The two elements may be spaced apart so that a slot is defined therebetween.

Slot.

Each jaw may include one or more slots. The slot may function to provide a passageway or area for one or more features of the instrument to be located. For example, a cut blade may be located in the slot. The slot may be substantially free of features or obstructions so that the cut blade can be located therein. For example, while the instrument according to the teachings herein includes one or more tissue stops and/or struts, the tissue stops and/or struts are arranged to not block the cut blade so that the cut blade can be translated, repositioned, or otherwise moved in the slot. That is, the tissue stops or portions thereof may be offset or arranged to a side of the slot.

The slot may be centered upon a central plane or axis of a jaw or the jaw assembly, or the slot may be offset or laterally spaced apart from a longitudinal axis to one side of the jaw or jaw assembly. Preferably, a center plane of the slot is free of any tissue stop. The tissue stops may be arranged along a medial plane that is offset from the central plane or axis so as to not interfere with the reciprocating cut blade, which may be centered upon the central plane. However, in some configurations, a tissue stop may be located along the center plane or axis of a slot, however, the cut blade is arranged along an edge or another plane of the slot that is not the center plane, for example, along a lateral or medial edge of the slot.

Arcuate Section.

The one or more jaws or jaw elements may include one or more arcuate sections. The one or more arcuate sections may cooperate with the tubular member to move the jaw assembly, the one or more jaws, or both between an open and closed position. The arcuate sections may be at least partially flexible and/or resilient so that the jaw assembly, the one or more jaws, or both can be moved, bent, pivoted, or the like when a pressure or force is applied thereto. When the pressure or force is released or removed, the arcuate sections, the jaw assembly, the jaws, or a combination thereof can move, bend, or relax back to an initial, steady state position.

The one or more arcuate sections can be any feature that is at least partially taller, wider, and/or larger than the tubular member, an inner portion of the tubular member, an opening of the tubular member (e.g., the distal opening), or a combination thereof. For example, the one or more raised or arcuate sections can be a thickened portion of the jaws or jaw elements or a projection attached to one or both of the jaws. The one or more arcuate sections may be a section that draws away from or extends away from a corresponding gripping section of the same jaw. Therefore, in electrosurgical forceps, an anatomical feature that is placed too far in a proximal direction between the jaws and is therefore located or positioned between the actuate sections may not be coagulated. Then, passing a non-energized cut blade through a non-coagulated anatomical feature may undesirably cause bleeding and/or trauma to the anatomical feature. Thus, the need for one or more tissue stops between the jaws is desirable to ensure that the anatomical feature is not placed too far in a proximal direction and outside of the energized features of the jaw assembly.

In some configurations, however, rather than a jaw assembly that flexes and bends between the open and closed positions by applying or removing a force from one or more of the arcuate sections, the jaw assembly may include a hinge or pivot mechanism for pivoting the jaw assembly between the closed and open positions. In these hinge or pivot type configurations, one or more of the jaws may be rigid bodies or links. In these configurations, one or more tissue stops between the jaw assembly may advantageously prevent an anatomical feature from being positioned too far in a proximal direction, thus preventing the anatomical feature from being pinched in the hinge or pivot mechanism during the opening and closing of the jaw assembly.

Anchoring Section.

The one or more jaws or jaw assembly may include one or more anchoring sections. The one or more anchoring sections may function to anchor, attach, or connect the jaws, the jaw assembly, or both to the hand piece. The anchoring sections may be connected to one or more anchoring rods. The anchoring section may be integrally formed with the anchoring rod, or may be connected thereto via any suitable method, such as welding, soldering, adhesives, stamping, etc. The anchoring rods may be connected to one or more mechanisms in the hand piece, so that when a user actuates one or more user controls, the mechanisms, the anchoring rods, and therefore the jaws and/or jaw assembly is moved. The anchoring rods may be connected to one or more electrodes. The anchoring rods may be electrically conductive. The anchoring rods may be in electrical communication with the power source. For example, at their distal ends, the anchoring rods may be connected to corresponding electrodes, and at their proximal ends the anchoring rods may be in communication with the power source, one or more electrical leads, wires, or a combination thereof. Preferably, the anchoring rods may be insulated from one another so that a short between the anchoring rods is prevented.

Gripping Section.

The one or more jaws may include one or more gripping sections. The gripping sections may function to effect an object or anatomical feature manipulate. A gripping section may be located at or near a distal region of a jaw. A gripping section may be located between a distal end of a jaw and a corresponding distal end of an arcuate section.

A gripping section may include one or more areas having teeth, no teeth, projections, or a combination thereof. The one or more teeth or projections may be formed or cut into the jaw or gripping section by a suitable process or method, such as by grinding, electrical discharge machining, stamping, coining, etc. A gripping section may include one or more troughs between the teeth to separate one tooth from another. The one or more teeth may have sharp points to assist in grasping an anatomical feature. Alternatively, or in addition, the one or more teeth may have flattened tops to distribute forces associated with grasping forces so that the object or tissue, especially vessel walls, are not punctured or otherwise damaged when an object, vessel, or tissue is between the jaws in the closed position.

A gripping section may be electrically conductive. That is, a gripping section may include one or more electrically conductive sections. The electrically conductive section may function to pass one or more therapy signals or currents between the gripping section, electrically conductive section, an object, the anatomy, or a combination thereof. The electrically conductive section may be or include an electrode or may be in communication with a power source. The electrically conductive may be an entire portion of the gripping section. That is, the electrically conductive sections may extend in an area or region between a distal tip of a jaw and a distal portion of an arcuate section. In other configurations, the electrically conductive sections may comprise a smaller area or section than the entire gripping section. Preferably, the instrument is adapted to pass opposing bipolar voltages to the opposing gripping sections to provide sealing or coagulation of an anatomical feature located between the gripping sections so that the instrument can function as bipolar forceps.

A gripping section may include one or more insulated sections or non-electrically conductive sections. The one or more insulated or non-electrically conductive sections may be insulated or otherwise not connected to an electrode or power source. Accordingly, the one or more non-electrically conductive sections may be unable or restricted from passing a therapy current between the jaws, an object, the anatomy, or a combination thereof.

The gripping section may comprise a plate. The plate may be fabricated from an electrically conductive material, such as sheet metal. The plate may be an electrode. The plate may be in electrical communication with the power source, and may function to pass a therapy current from the power source to or through an anatomical feature to another electrical conductor or plate to electrically effect an anatomical feature located between the plates. The plate may be assembled onto an insulator, and the insulator may then be attached or assembled onto the jaw. The plate may include one or more features of the gripping section discussed above (i.e., teeth, no teeth, etc.).

Cut Blade.

The instrument may include one or more cut blades. The cut blade may function to cut an object or anatomical feature of interest, such as a vessel or tissue, for example. The cut blade may be a cutting blade or a scalpel. The cut blade may not be connected to the power source or is electrically isolated from the power source, thus, the cut blade may be free from passing an electrical therapy current to effect an anatomical feature. Thus, the cut blade may be a cold cut blade or a mechanical cut blade. The cut blade may be moved or reciprocated within the slot by moving or manipulating one or more of the user controls on the hand piece discussed above. The cut blade can be moved or extended to cut an anatomical feature captured between the jaw assembly (e.g., when the jaw assembly is in a closed or clamping position). The cut blade may cut an anatomical feature after the anatomical feature is clamped and/or coagulated or sealed between the jaws of the jaw assembly. The cut blade may also cut an anatomical feature when the jaw assembly is in the open position.

The cut blade can be located between the jaws. The cut blade can be located in a slot between two opposing jaw elements. As was discussed above, the cut blade may be centered in a slot axis. The cut blade may be offset to one side of the slot axis (i.e., laterally offset from the center slot axis). The cut blade may be offset the slot axis towards one of the jaw elements.

Jaw Shroud.

The jaw assembly may include one or more jaw shrouds. The jaw shroud may function to reinforce or stiffen the gripping section of a jaw. Preferably, the jaw shroud reinforces or stiffens a griping section of a jaw that is bendable and flexible. Advantageously, a jaw shroud may provide for an entire jaw to be bendable or flexible so that the jaw can be bent or flexed between a closed and open position as was discussed above, while the gripping sections are made rigid or not bendable as the rest of the jaw so that an anatomical feature can be securely gripped between the jaws without the jaw deflecting or bending while in the closed position. The jaw shroud may function to provide the jaw assembly with a substantially uniform grasping or gripping pressure or force in the gripping section. The jaw shroud may function to overcome beam deflection in one or both of the jaws when the jaw assembly is in a closed position or is being moved into the closed position especially when an object, vessel, or tissue is located between the jaws.

A jaw shroud may be attached to one or both of the jaws. That is, a jaw shroud can be attached to an upper jaw, a lower jaw, or both jaws. The jaw shroud may be attached to a jaw in any suitable manner. For example, the jaw shroud may be bonded or over-molded onto a jaw. For example, the jaw shroud can be slipped-on or slipped-over a distal end of a jaw. For example, the jaw shroud may be attached, connected, interlaced, welded, ultrasonically welded, staked, adhered, or a combination thereof onto a jaw. For example, the jaw shroud can be snapped into or onto a channel, groove, or projection in or on a corresponding jaw. The jaw shroud can include one or more connecting features that may cooperate with one or more undercut features on the jaw. The one or more connecting features, undercut features, or both can be welded or melted together to prevent or restrict removal or separation of the jaw shroud and the jaw. The one or more connecting features, undercut feature, or both may be one or more metal or plastic mating projections, grooves, nubs, posts; mating male and female dovetail sections, or other like features suitable for connecting the spine and the shroud.

In some configurations, the jaw shroud may be irreversibly attached to the jaw. Irreversibly attached may mean that the jaw cannot be separated from the jaw without substantially damaging the jaw shroud and/or the jaw. In some configurations, the jaw shroud may be integrally formed with the jaw.

The jaw shroud may be fabricated from a suitable material. Preferably, the jaw shroud is fabricated from a material that is suitable for use in medical procedures, such as metal and/or plastic, for example. The jaw shroud may be formed by any suitable process, such as stamping, metal injection molding (MIM), or plastic injection molding, for example. The jaw shroud may be thermally insulating so that a thermal barrier can be provided between the jaws, the jaw assembly, or both. A thermally insulting shroud may be preferred in some applications so that thermal spread is limited or reduced. The jaw shroud may be electrically insulating to prevent an electrical short when the instrument is used in electrosurgery.

Tissue stops.

The instrument, the jaws, the jaw shroud, or a combination thereof may include one or more tissue stops. Advantageously, the one or more tissue stops may function to block, prevent, or at least restrict an object or anatomical feature from being positioned or extending beyond a proximal end of a gripping section; beyond a proximal end of an electrically conductive section; or both. Advantageously, the one or more tissue stops may block, prevent, or restrict an anatomical feature or object from extending into a hinge, joint or pivot mechanism of the jaw assembly thus reducing chances of an anatomical feature being pinched therein. Advantageously, the one or more tissue stops may block, prevent or restrict an anatomical feature from extending into an area where the arcuate sections are (i.e., beyond a distal end of the arcuate sections). Advantageously, the one or more tissue stops may block, prevent, or restrict an anatomical feature from extending too far in a proximal direction and off of a gripping section thus ensuring that a sufficient gripping force is applied on a desired portion of the anatomical feature. Advantageously, the one or more tissue stops may block, prevent or restrict an anatomical feature or object from extending too far in a proximal direction and off of an electrically conductive section thus ensuring that an entire desired portion of the anatomical can be electrically coagulated during an electrosurgical procedure.

A tissue stop may be a feature that extends from one jaw, griping section, or jaw shroud towards another jaw, gripping section, or jaw shroud. A tissue stop may be attached to or made integral with a jaw, gripping section, jaw shroud, or a combination thereof. A tissue stop may be, for example, a projection, a protrusion, a cantilevering member or section, or a combination thereof. The tissue stop may be generally flat, having aspect ratios that it is generally longer than it is wide, and generally wider than it is thick. A tissue stop may have a constant thickness so the two sides may be generally parallel to each other. Alternatively, the thickness may taper slightly along the length of the tissue stop. In either event, a tissue stop will have a first side and a second side that are, or nearly are, parallel. Between the sides and along the body of the tissue stop there is a central plane, about which the tissue stop may be generally symmetric.

One or more of the tissue stops may be made from the same material as a jaw, jaw shroud, gripping section, or a combination thereof. The one or more tissue stops may be electrically conductive. However, preferably, if the tissue stops are electrically conductive, the tissue stops are free from participating, or do not particulate, in an electrical circuit for electrosurgically effecting an anatomical feature. One or more of the issue stops may be made from an electrically insulating, or non-conductive material. Thus, one or more of the tissue stops may be electrically non-conductive.

One or more of the tissue stops may be located proximal to a gripping section. One or more of the tissue stops may be located in a gripping section. That is, a tissue stop may be located between a proximal and distal end of a gripping section. One or more of the tissue stops may be located distal of an arcuate section.

A tissue stop may be located along an outside edge or lateral plane of a jaw, jaw shroud, or both. A tissue stop may be located along an inside edge or medial plane of a jaw, jaw shroud, or both. One or more tissue stops that are located at or along an outside edge or lateral plane of a jaw or jaw shroud may cooperate with one or more tissue stops located along an inside or medial plane of a jaw, jaw shroud, or both to provide additional blocking and control of an anatomical feature from extending beyond a proximal end of a gripping section, beyond a distal end of an arcuate section, or both compared to if a tissue stop is located only at or along an outside edge or lateral plane of a jaw. That is, a tissue stop that is located only at a lateral or outside edge of the jaw may not be effective in restricting, preventing, or blocking an anatomical feature from extending proximally beyond a griping or electrically conductive section if, for example, the anatomical feature is placed in the jaw assembly in a location that is offset or favors an opposing lateral or outside edge of the jaw where the tissue stop cannot contact the anatomical feature to provide the blocking function. Similarly, a jaw that includes tissue stops located at both opposing lateral edges of a jaw or jaw shroud may not be effective in restricting, preventing, or blocking an anatomical feature from extending proximally beyond a griping or electrically conductive section if, for example, the anatomical feature is thin or narrow and is able to pass freely between the tissue stops without the tissue stops contacting the anatomical feature to provide the blocking function.

One or more tissue stops may be located on an upper jaw or jaw shroud and extend towards a lower jaw or jaw shroud, and one or more tissue stops may be located on a lower jaw or jaw shroud and extend towards an upper jaw or jaw shroud.

A jaw assembly having a plurality of tissue stops may include tissue stops that are the same height or different heights. In some configurations, a height of the tissue stops on an upper jaw or jaw shroud may be larger than a height of the tissue stops on the lower jaw, or vice versa. Two or more tissue stops may be aligned with one another. That, is a center plane of the tissue stops may be coplanar, aligned, or centered about the same plane, and one tissue stop may be located distal relative to the other tissue stop(s) to prevent the tissue stops from interfering with one another, or to keep the tissue stops free from interfering with one another when the jaw assembly is in the closed position or being moved into the closed position.

In some configurations, the one or more tissue stops may be received in a notch, gap, or slot of an opposing jaw or jaw shroud so that the jaw assembly may be moved into a closed position without the tissue stops interfering with the closing. In the closed position, the one or more tissue stops may be received into the slot defined between the two opposing jaw elements. Preferably, in the closed position, the one or more tissue stops are received into the slot, but are located along an edge of the slot so as to not interfere with a cut blade, or other element that may also be located in the slot.

In some configurations, a height of one or more of the tissue stops may be short enough to not require the tissue stop to be received in a notch, gap, or slot of an opposing jaw or jaw shroud when the jaw assembly is moved into a closed position. In these configurations, preferably, tissue stops are located on both of the opposing jaws or jaw shrouds. In these configurations, preferably, a height of the tissue stops extending from each jaw or jaw shroud is still tall enough to overlap one another when the jaw assembly is in the open position. Such an arrangement will still advantageously restrict or prevent an anatomical feature from passing or extending proximally beyond the tissue stops and/or the gripping sections.

Overlap of a tissue stop may mean that when viewed from a side of the instrument or jaw assembly, and when the jaw assembly is in an open position, a free end of one tissue stop extends beyond a gripping surface of the opposing jaw. Overlap of tissues stops on opposing jaws may mean that when viewed from a side of the instrument or jaw assembly, and when the jaw assembly is in an open position, a free end of a tissue stop on one jaw extends beyond a free end of a tissue stop on the opposing jaw.

Strut.

The instrument, the one or more jaws, the one or more jaw shrouds, the one or more of the tissue stops, or a combination thereof may include one or more struts. A strut may function to provide stability for one or more of the tissue stops. That is, a tissue stop may contact a strut when the jaw assembly is in the open position, in the closed position, or is being moved into closed position such that the tissue stop rests against the strut. A tissue stop may be restricted or prevented from being moved, flexed, or pushed in a proximal direction as a result of it resting on a strut. For example, when an anatomical feature is being positioned between the opposing jaws, the anatomical feature may contact the tissue stop, and then push the tissue stop in a proximal direction. The tissue stop may however, be restricted from being moved or pushed in the proximal direction due to it resting or abutting against the strut, which may thus provide stability to the tissue stop. One or more struts may extend from a lateral or outside edge of a tissue stop, from a medial or inside edge of a tissue stop, or both. A strut located on a lower tissue stop may provide stability for a tissue stop located on an upper jaw or shroud and/or a struct located on an upper tissue stop may provide stability for a tissue stop located on a lower jaw or lower shroud. The strut may be a projection or extension from a tissue stop, a jaw, a jaw shroud or a combination thereof.

A strut may also function to provide additional tissue blocking surface area. That is, a strut may also function in the same or similar manner as a tissue stop to prevent, block, or restrict an anatomical feature from extending beyond a proximal end of a gripping section or electrically conductive section. For example, the struct may prevent a thin anatomical feature from passing between two adjacent or laterally located tissue stops. Alternatively, a strut may function independently to block an anatomical feature from being positioned proximal to the gripping section by extending laterally from a tissue stop, medially from a tissue stop, or both. However, preferably, a strut does not obstruct a cut blade slot so that the cut blade can be moved or reciprocated to cut the anatomical feature. When the jaw assembly is moved into a closed position, the struct may be received into or fit into an arcuate section on the opposing jaw so as to not interfere with closing of the jaw assembly.

As used throughout this description, "centered on" refers to a plane that is aligned with, co-planar with, centered on or about, or the same as another plane. For example, the tissue stop may be centered on a central plane of the jaw assembly. This refers to the central plane of the tissue stop being aligned with, coplanar with, centered on or about, or the same as the central plane of the jaw assembly and thus a side of the tissue stop being located on each side of the central plane of the jaw assembly and on each side of the tissue stop.

As used throughout this description, "medial plane" refers to a plane that is not a lateral plane. "Medial" and "lateral" are terms of relative position. Therefore, if a first plane is closer to a center plane than a second plane, the first plane is "medial." Any plane that is closer to an outside is "lateral plane." Therefore, if the second plane is closer to an outside plane than the first plane, the second plane is "lateral." Accordingly, a plane that is at an outer edge or outer side of a jaw is a "lateral plane of the jaw". Of course, there is a lateral plane at the other lateral plane or outer edge of the jaw. Any and all planes (that are generally parallel these planes) and between them is a "medial plane of the jaw."

"Medial side of the tissue stop." Each tissue stop will have one side closer to the central axis of the slot (the medial side or plane of the tissue stop) and one side further away from the central axis of the slot (the lateral side or plane of the tissue stop). Notably, in this definition, "medial"/"lateral" does not necessarily need to be defined relative to a true center plane of the width of the jaw assembly or jaws. For example, if the center slot were profoundly skewed to the left side so that a tissue stop placed on the right edge of the slot existed entirely on the left side of the true center plane of the jaw assembly or jaws, "medial" would be the left side of the tissue stop and "lateral" would be the right side of the tissue stop.

"Juxtaposed" as used herein means that an edge or side of a particular feature is arranged or located adjacent or next to a side or edge of another feature. A gap may exist between features that are juxtaposed, or the features may be arranged "line-to-line" with little to no gap therebetween. Juxtaposed may mean a side, plane, or feature is next to another side plane or feature, but is/are able to slip past one another.

FIG. 1 illustrates an instrument 10. The instrument 10 includes a tubular member 12, a jaw assembly 14, and a hand piece 16. The jaw assembly 14 comprises a first jaw 18 and a second jaw 20. The hand piece 16 includes one or more user controls, including a lever 22, a trigger 24, a wheel 26, and a button 28. The instrument 10 may be in communication with a power source 30.

Figure 2:
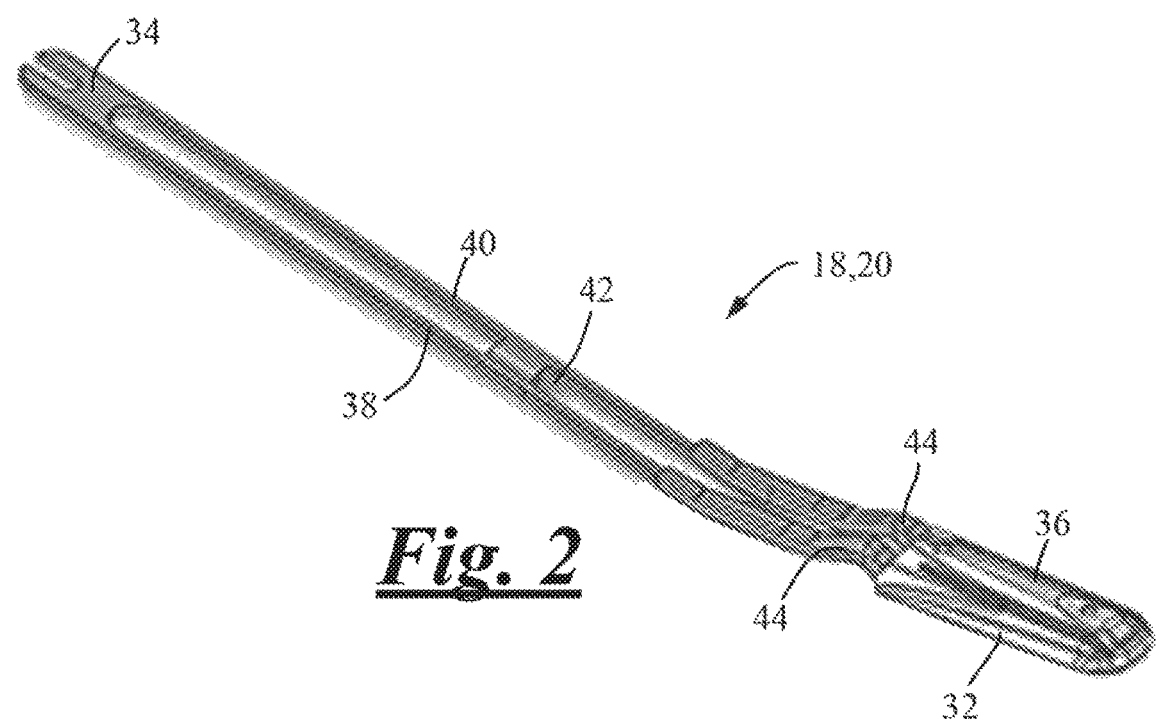
FIG. 2 is a perspective view of a jaw element of a jaw assembly.

FIG. 2 illustrates the first jaw 18, which may also be the second jaw 20. The jaw 18, 20 includes a gripping section 32 and an anchoring section 34. The jaw 18, 20 includes a jaw shroud 36. The jaw 18, 20 includes a pair of spaced apart jaw sections 38, 40. A slot 42 is defined between the two jaw sections 38, 40 and extends to a distal end of the jaws 18, 20. Each jaw section 38, 40 includes an arcuate section 44.

In the following FIGS. 3-7, reference will be made to the various features of the jaws 18, 20 and/or the jaw sections 38, 40. It is understood that an "a" following a reference numeral corresponds to the features associated with jaw 18, and a "b" following a reference numeral corresponds to the features associated with jaw 20.

Figure 3:
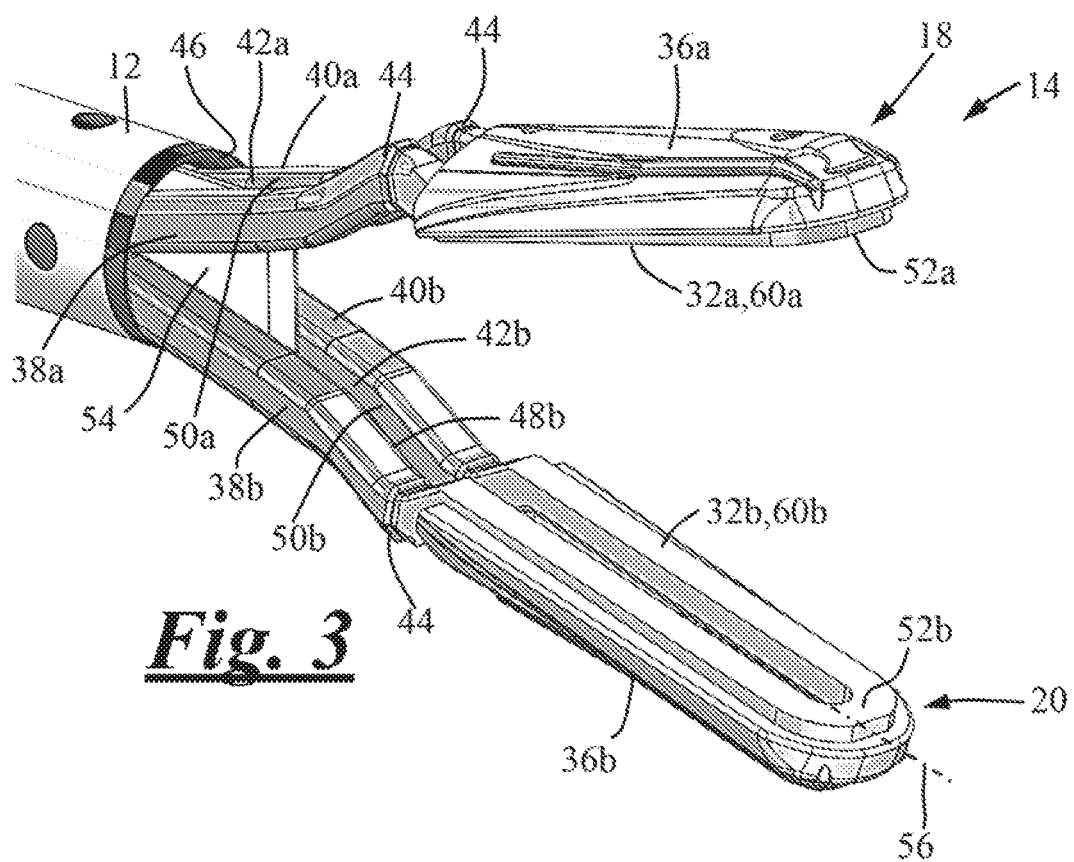
FIG. 3 is a perspective view of a jaw assembly.

FIG. 3 illustrates the jaw assembly 14. The jaw assembly 14 is in the open position. The tubular member 12 includes a mouth or distal opening 46. Moving the tubular member 12 in a distal direction away from the hand piece 16 and into contact with the arcuate sections 44 and then onto the arcuate sections 44 causes one or both of the opposing jaws 18, 20 to move or flex towards one another thus moving the jaw assembly 14 from the open position to a closed position (not shown).

Alternatively, or additionally, moving the jaw assembly 14 in a proximal direction towards the hand piece 16 so that the arcuate sections 44 contact the mouth or distal opening 46 of the tubular member 12 also functions to move or flex one or both of the jaws 18, 20 towards one another thus moving the jaw assembly 14 from the open position to the closed position.

Of course, when the jaw assembly 14 is in the closed position, moving the tubular member 12 proximally relative to the hand piece 16 and/or moving the jaw assembly 14 distally relative to the hand piece 16 functions to allow one or both of the jaws 18, 20 to move or flex away from one another so that the jaw assembly moves or flexes from the closed position to the open position.

With continued reference to FIG. 3, jaw section 38b includes a medial plane or inside edge 48b, and jaw section 40b includes a medial plane or inside edge 50b. The slot 42b may defined by two opposing lateral edges, which may be edges 48b and 50b of jaw sections 38b, 40b. The slot 42b may centered about a center axis or plane 56 of the jaw 20 that extends between the edges 48b, 50b.

Similarly, jaw section 38a includes a medial plane or inside edge 48a (see FIG. 4b) and jaw section 40a includes a medial plane or inside edge 50a. The slot 42a may be defined between two opposing lateral edges, which may be the two aforementioned edges 48a, 50a of jaw elements 38a, 40a. The slot 42a may centered about a center axis or plane 56 of the jaw 18 that extends between the edges 48a, 50a. Slot 42a and 42b may be the same plane or coplanar. Jaw sections 38a, 40a are joined together at a distal nose portion 52a, and the jaw sections 38b, 40b are joined together at a distal nose portion 5b.

A cut blade 54 is received in the slots 42a, 42b, and is moveable therein. For example, the cut blade 54 is moveable by manipulating one of the user controls on the hand piece 16 so that the cut blade 54 moves towards and away from the distal nose portions 52a, 52b. The gripping section 32a, 32b of one or both of the jaws 18, 20 may be electrically conductive (i.e., electrically conductive sections), or, one or both of the gripping sections 32a, 32b may include an electrode 60a, 60b in electrical communication with the power source 30 (FIG. 1). Each jaw 18, 20 includes a respective jaw shroud 36a, 36b.

It is understood that any of the tissue stops illustrated in FIGS. 4a-7, or described in this disclosure, may be added to the jaw assembly illustrated in FIG. 3. Similarly, it is understood that the cut blade 54 illustrated in FIG. 3 may be added to any of the jaw assemblies illustrated in FIGS. 4a-7, or described in this disclosure.

FIGS. 4a and 4b illustrate the jaw assembly 14. Each jaw 18, 20 includes a respective jaw shroud 36a, 36b. Each jaw shroud 36a, 36b includes a respective tissue stop 64a, 64b. Tissue stop 64a extends from jaw 18 to or towards jaw 20, and tissue stop 64b extends from jaw 20 to or towards jaw 18. Each tissue stop 64a, 64b is located proximal to the respective gripping section 32a, 32b. The tissue stops 64a, 64b overlap each other when the jaw assembly 14 is in the open position, and cooperate to restrict, prevent, or block an anatomical feature from going beyond a proximal end 62a, 62b of the respective gripping section 32a, 32b. Thus, the anatomical feature remains in a position between the gripping sections 32a, 32b so that the entire anatomical feature can be effected or coagulated between the gripping sections 32a, 32b. Without the tissue stops 64a, 64b, a portion of the anatomical feature may inadvertently or unintentionally extend beyond one or both of the proximal ends of the gripping sections 32a, 32b, which may result in that portion of the anatomical feature not being coagulated. When the cut blade 54 of FIG. 3 is extended or advanced through the uncoagulated portion of the anatomical feature, the anatomical feature may undesirably bleed.

At least one of the tissue stops, for example, tissue stop 64b includes a strut 66. The strut 66 extends laterally from a lateral or outside surface 74b of the tissue stop 64b.

As perhaps best illustrated in FIG. 4b, the tissue stops 64a, 64b are centered on a medial plane 68 of the jaws 18, 20. The medial plane 68 is offset from a central plane or axis 56 of the jaws 18, 20 or jaw assembly 14. The central plane or axis 56 may also be a central plane or axis of the slots 42a, 42b, but need not be (See FIG. 5, for example). The medial plane 68 is offset from a lateral plane or outside edges 70a, 70b of jaw sections 38a, 38b. The medial plane 68 is offset from a lateral plane or outside edges 72a, 72b of jaw sections 40a, 40b. The offset of the medial plane 68 may advantageously provide clearance for the cut blade to be reciprocated, which may occur along a longitudinal axis or a central plane of the jaw assembly.

With continued reference to FIG. 4b, a lateral plane or outside edge 74a of tissue stop 64a is juxtaposed, aligned with, or adjacent the medial plane or inside edge 48a of jaw element 38a. A lateral plane or outside edge 74b of tissue stop 64b is juxtaposed, aligned with, or adjacent the medial plane or inside edge 48b of jaw element 38b.

When the jaw assembly 14 is moved into the closed position, the lateral plane or outside edge 74a of tissue stop 64a is also juxtaposed, aligned with, or adjacent the medial plane or inside edge 48b of jaw element 38b. Similarly, when the jaw assembly 14 is moved into the closed position, the lateral or outside edge 72b of tissue stop 64b is also juxtaposed, aligned with, or adjacent the medial or inside edge 48a of jaw element 38a. According to this aforementioned arrangement of the tissue stops 64a, 64b, in the open and closed position of the jaw assembly 14, the slots 42a, 42b remain free of obstructions so that a cut blade 54 (FIG. 3) can extend through the gap 42. When the jaw assembly 14 is moved into the closed position, the tissues stop 62a is at least partially received into slot 42b, and tissue stop 62b is at least partially rescued into slot 42a.

While FIG. 4b illustrates the slots 42a, 42b are generally centered about a center axis or plane 56 of the jaws 18, 20 or jaw assembly, FIG. 5 clarifies that the slots 42a, 42b need not be centered about the center axis or plane 56 of the jaws 18, 20.

More specifically, FIG. 5 illustrates that a center axis or plane 76 of the slots 42a, 42b may be offset or skewed from the enter axis or plane 56 of the jaws 18, 20 or jaw assembly in a direction towards jaw section 38. It is understood that while not illustrated, the center axis 76 or plane of the slots 42a, 42b can be offset or skewed from the center axis or plane 56 towards the other jaw section 40.

Moreover, each tissue stop 64 has thickness that includes a first side 80 and a second side 82, which are centered about a tissue stop axis or plane 82, which may also be the medial plane 68 of the jaws 18, 20 or jaw assembly 14. Relative to the center axis or plane 56 of the jaw 18, 20, the first side 78 can be defined as a lateral or outside edge, and the second side 80 can be defined as a medial or inside edge. However, relative to the central axis or plane 76 of the slot 42, the first side 78 can be defined as s a medial or inside edge, and the second side 80 can be defined as a lateral or outside edge.

Figure 6:
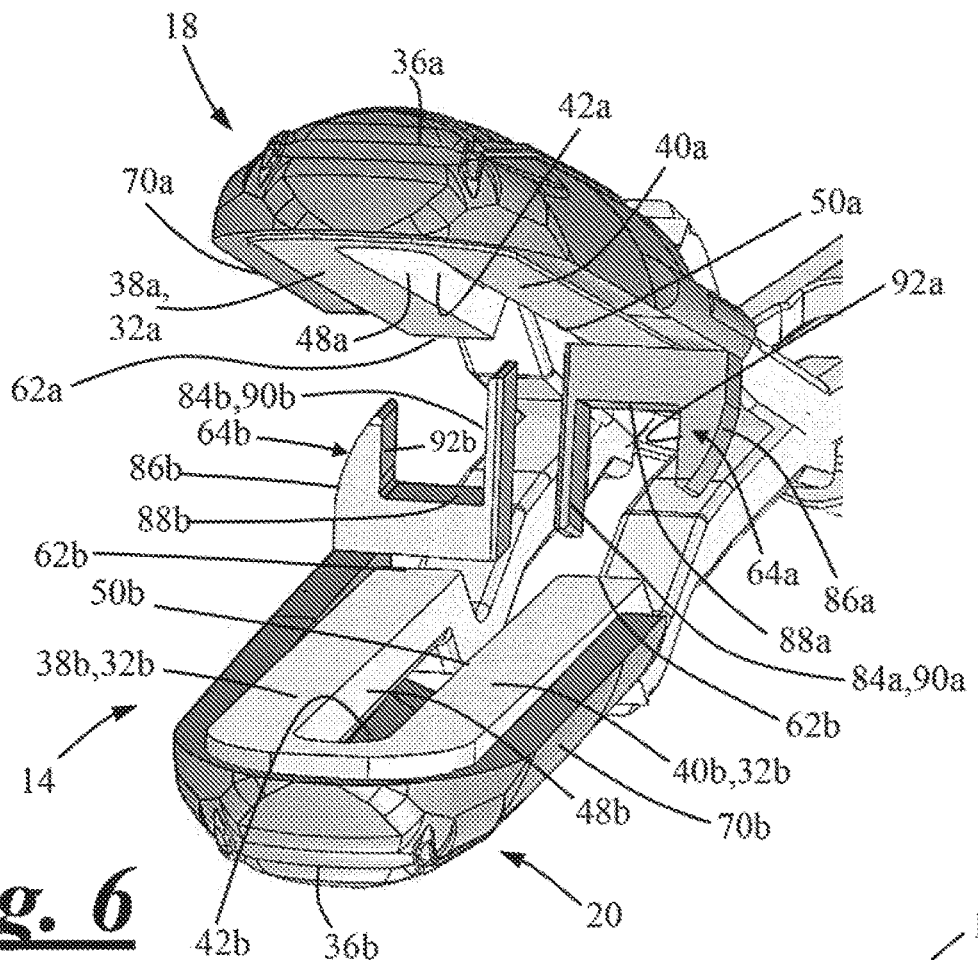
FIG. 6 is a perspective view of the jaw assembly.

FIG. 6 illustrates the jaw assembly 14. Each jaw 18, 20 includes a respective jaw shroud 36a, 36b, and each jaw shroud 36a, 36b includes a respective tissue stop 64a, 64b. Each jaw 18, 20 includes a gripping section 32a, 32b. Each jaw 18, 20 includes a slot 42a, 42b defined between two opposing corresponding lateral edges 48a, 50a and 48b, 50b.

Each tissue stop 64a, 64b is generally U-shaped and includes an interior, inner, or medial leg 84a, 84b and an exterior, outer, or lateral leg 86a, 86b, with a channel or gap 88a, 88b defined between the interior 66a, 66b and exterior legs 68a, 68b. The interior, inner, or medial legs 84a, 84b are centered on a medial plane of the jaws 18, 20, which is offset from a center axis or plane of the jaws 18, 20.

The tissue stops 64a, 64b are located proximal to gripping sections on the first jaw 18 and second jaw 20. The tissue stops 64a, 64b may cooperate to restrict, prevent, or block an anatomical feature from going beyond a proximal end 62a, 62b of the respective gripping section 32a, 32b. Thus, the anatomical feature remains between the gripping sections 32a, 32b so that the entire anatomical feature can be effected, grasped, clamped, and/or coagulated between the gripping sections 32a, 32b. Without the tissue stops 64a, 64b, a portion of the anatomical feature may extend beyond the proximal ends of the gripping sections 32a, 32b, for example into the areas of the arcuate sections, which may result in that portion of the anatomical feature not being coagulated. When the cut blade 54 of FIG. 3 is extended or advanced through the uncoagulated portion of the anatomical feature, the anatomical feature may undesirably bleed.

The interior, inner, or medial leg 84a of tissue stop 64a includes an exterior edge or medial plane 90a that is coplanar with or aligned with the medial plane or inside edge 50a of jaw section 40a. In the closed position, at least a portion of the interior, inner, or medial leg 84a extends into the slot 42b and at least a portion of the exterior edge or lateral side or medial plane 90a of the interior, inner, or medial leg 84a is juxtaposed with the medial plane or inside edge of jaw section 40b of slot 42b.

When the jaw assembly 14 is in the open position, the inner leg 84a of tissue stop 64a and at least a portion of the outer leg 86a overlaps the jaw 20b at a position that is proximal to an end 62a of gripping section 32a of the first jaw 18, at a position proximal to an end 62b of the gripping section 32b of the second jaw 20 or both.

The exterior, outer, or lateral leg 86a of tissue stop 64a includes an interior edge or lateral plane 92a. In the closed position, the exterior, outer, or lateral leg 86a remains on an outside of the jaw shroud 36b and the interior edge or lateral plane 92a is juxtaposed with an outside surface or plane 70b of the jaw 20 or jaw shroud 36b. In the closed position, the channel 88a is adapted to receive at least a portion of the jaw element 40b and/or gripping section 32b.

The interior or medial leg 84b of tissue stop 64b includes an exterior edge or medial plane 90b that is coplanar with or aligned with the medial plane or inside edge 50b of jaw section 38a. In the closed position, the interior leg 84b extends into the slot 42a and the exterior edge or medial plane 90b of the interior or medial leg 84b is juxtaposed with the medial pane or inside edge 48a of jaw section 38a. The exterior, outer, or lateral leg 86b of tissue stop 64a includes an interior edge or lateral plane 92b. In the closed position, the exterior or lateral leg 86b remains on an outside of the jaw shroud 36a and the interior edge or lateral plane 92b is juxtaposed with an outside surface or plane 70a of the jaw 18 or jaw shroud 36a. In the closed position, the channel 88b is adapted to receive at least a portion of the jaw element 38a and/or gripping section 32a.

According to this aforementioned arrangement of the tissue stops 64a, 64b, in the open and closed position of the jaw assembly 14, the slots 42a, 42b remain free of obstructions so that a cut blade 54 (FIG. 3) can extend through the gap 42.

Figure 7:
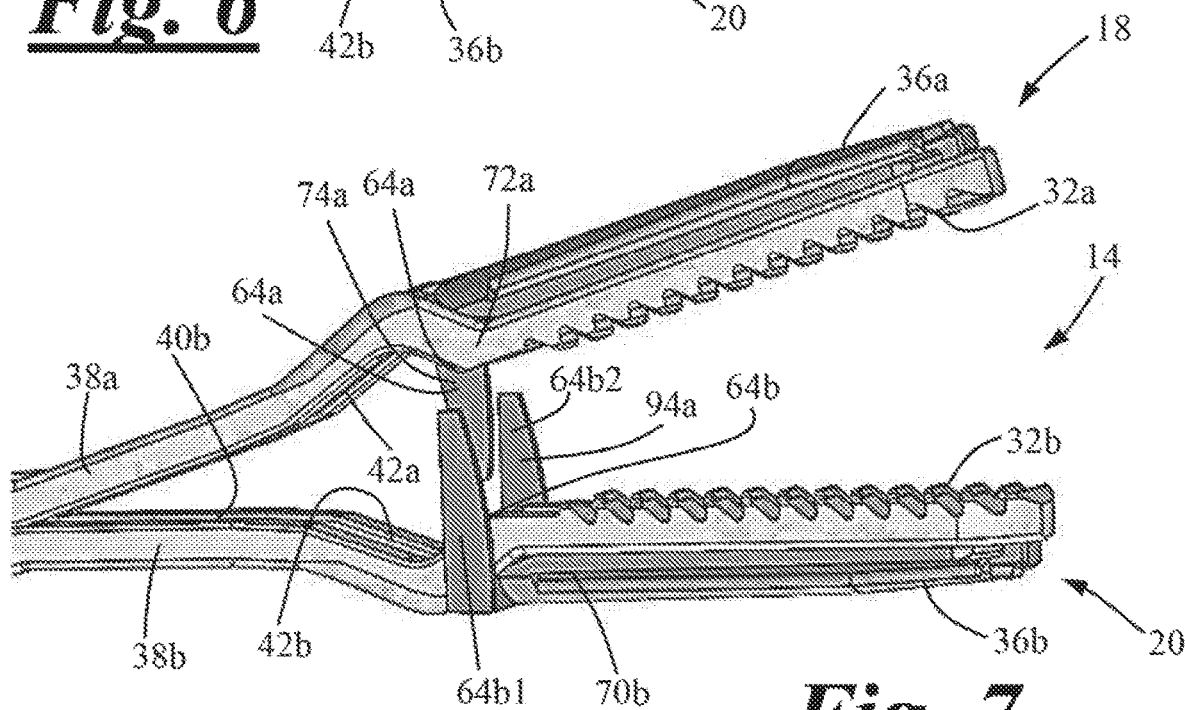
FIG. 7 is a perspective view of the jaw assembly.

FIG. 7 illustrates the jaw assembly 14. Each jaw 18, 20 includes a respective jaw shroud 36a, 36b. Jaw shroud 36a includes a tissue stop 64a that extends from jaw 18 to or towards jaw 20, and jaw shroud 36b includes tissue stops 64b1 and 64b2 both of which extend from jaw 20 to or towards jaw 20. The tissue stops 64a, 64b1, and 64b2 are located proximal to gripping sections on the first jaw 18 and second jaw 20.

Tissue stop 64a is centered on a medial plane of the jaws 18, 20 which is offset from a center axis or plane of the jaws 18, 20. Tissue stop 64a includes a lateral plane or outside edge 74a that is aligned with a medial pane or inside edge (not shown, See FIG. 4b) of jaw section 38a. In the closed position, the lateral plane or outside edge 74a is aligned with or juxtaposed with the medial plane or inside edge of jaw section 38b (not shown, See FIG. 5b).

Tissue stop 64b1 includes a medial plane or inner edge (not shown) that is aligned with the lateral plane or outside edge 70b of the jaw section 38b. In the closed position, the medial or inner edge of tissue stop 64b1 is aligned with or juxtaposed with the lateral plane 70a or outside edge 72a of jaw section 38a. Tissue stop 64b2 includes a medial plane or inner edge 94a that is aligned with the lateral plane or outside edge (not shown) of the jaw section 38b. In the closed position, the medial or inner edge 94a of tissue stop 64b2 is aligned with or juxtaposed with the lateral plane or outside edge (not shown) of jaw section 40a.

The tissue stops 64a, 64b1, and 64b2 may cooperate to restrict, prevent, or block an anatomical feature from going beyond a proximal end 62a, 62b of the respective gripping section 32a, 32b. Thus, the anatomical feature remains between the gripping sections 32a, 32b so that the entire anatomical feature can be effected, grasped, clamped, and/or coagulated between the gripping sections 32a, 32b. Without the tissue stops 64a, 64b, a portion of the anatomical feature may extend beyond the proximal ends of the gripping sections 32a, 32b, for example into the areas of the arcuate sections, which may result in that portion of the anatomical feature not being coagulated. Medial placement of a tissue stop in the jaw assembly may be more effective at restricting, preventing, or blocking an anatomical feature from extending beyond a proximal end 62a, 62b of the respective gripping section 32a, 32b than only a laterally placed tissue stop because a tissue stop that is located only at a lateral or outside edge may not be effective in restricting, preventing, or blocking an anatomical feature that is placed in the jaw assembly, but offset towards an opposing lateral side of the jaws and out of the reach of the tissue stop. Moreover, tissue stops that are located at an outside or lateral edge may not be effective in blocking or preventing a thin or narrow anatomical feature from extending beyond da proximal end of the gripping section. When the cut blade 54 of FIG. 3 is extended or advanced through the uncoagulated portion of the anatomical feature, the anatomical feature may undesirably bleed.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The disclosures of all articles and references, including patent applications and publications, are incorporated by reference for all purposes.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. An instrument, comprising:
   forceps comprising:
   a jaw assembly comprising:
   i) a first jaw, the first jaw comprising a gripping section extending at least partially about a first medial blade slot; and
   ii) a second jaw, the second jaw comprising a gripping section extending at least partially about a second medial blade slot;
   wherein the jaw assembly is moveable between an open position and a closed position;
   wherein the first jaw includes a first tissue stop having at least portion that is received by the second medial blade slot when the jaw assembly is in a closed position, and
   the second jaw includes a second tissue stop that protrudes from the second jaw toward the first jaw.

2. The instrument of claim 1, wherein the instrument comprises a blade extendable distally beyond the first tissue stop into the first medial blade slot and the second medial blade slot when the jaw assembly is in a closed position.

3. The instrument of claim 1, wherein the first tissue stop is adapted to block an anatomical feature from extending proximally beyond a proximal end of the gripping section of the first jaw, a proximal end of the gripping section of the second jaw, or both.

4. The instrument of claim 1, wherein the first jaw is electrically conductive, the second jaw is electrically conductive, or both the first jaw and the second jaw are electrically conductive.

5. The instrument of claim 1, wherein the first tissue stop is electrically non-conductive.

6. The instrument of claim 1, wherein each of the first medial blade slot and the second medial blade slot are defined between two opposing lateral edges of a corresponding one of the first and second jaws.

7. The instrument of claim 1, wherein the second tissue stop is adapted to block an anatomical feature from extending proximally beyond a proximal end of the gripping section of the first jaw, a proximal end of the gripping section of the second jaw, or both.

8. The instrument of claim 1, wherein both the first tissue stop and the second tissue stop are centered on a medial plane of the first jaw.

9. The instrument of claim 8, wherein the first tissue stop is longitudinally offset from the second tissue stop such that the first tissue stop and the second tissue stop are free from interfering with one another when the jaw assembly is moved into the closed position.

10. The instrument of claim 9, wherein a distal tip of the first tissue stop extends a distal tip of the second tissue stop when the jaw assembly is in the open position so that an anatomical feature is blocked from extending proximally beyond a proximal end of the gripping section of the first jaw, the proximal end of the gripping section of the second jaw, or both.

11. The instrument of claim 1, further comprising a strut extending laterally from the first tissue stop away from the first blade slot.

12. The instrument of claim 1, wherein the first tissue stop is generally U-shaped and includes an inner leg, an outer leg, and a gap defined between the inner leg and the outer leg.

13. The instrument of claim 12, wherein when the jaw assembly is in the closed position, at least a portion of the gripping section of one of the first and second jaws is received by the gap of the tissue stop attached to the other of the first and second jaws.

14. The instrument of claim 12, wherein at least a portion of the inner leg is received in the second medial slot of the second jaw when in a closed position.

15. The instrument of claim 12, wherein the gap is configured to receive at least a portion of a raised gripping portion of the second jaw when in the closed position.

16. An instrument, comprising:
   forceps comprising:
   a jaw assembly comprising:
   i) a first jaw, the first jaw comprising a gripping section extending at least partially about a first medial blade slot; and
   ii) a second jaw, the second jaw comprising a gripping section extending at least partially about a second medial blade slot;
   wherein the jaw assembly is moveable between an open position and a closed position;
   wherein the first jaw includes a first tissue stop having at least portion that is received by the second medial blade slot when the jaw assembly is in a closed position,
   wherein the second jaw comprises a second tissue stop that protrudes from the second jaw toward the first jaw and a third tissue stop that protrudes from the second jaw toward the first jaw.

17. The instrument of claim 16, wherein the third tissue stop is adapted to block an anatomical feature from extending proximally beyond a proximal end of the gripping section of the first jaw, the proximal end of the gripping section of the second jaw, or both.

18. The instrument of claim 16, wherein the second tissue stop and the third tissue slop are located on opposing sides of the second blade slot of the second jaw.

19. An instrument, comprising:
   a forceps comprising:
   a jaw assembly comprising:
   i) a first jaw, the first jaw comprising a gripping section extending at least partially about a first medial blade slot; and
   ii) a second jaw, the second jaw comprising a gripping section extending at least partially about a second medial blade slot;
   wherein the jaw assembly is moveable between an open position and a closed position;
   wherein the first jaw includes a first tissue stop having at least portion that is received by the second medial blade slot when the jaw assembly is in a closed position,
   wherein the first tissue stop is generally U-shaped and includes an inner leg, an outer leg, and a gap defined between the inner leg and the outer leg, wherein the gap is configured to receive at least a portion of a raised gripping portion of the second jaw when in the closed position.

* * * * *